United States Patent [19]
Pigott

[11] Patent Number: 5,156,620
[45] Date of Patent: Oct. 20, 1992

[54] INTRALUMINAL GRAFT/STENT AND BALLOON CATHETER FOR INSERTION THEREOF

[76] Inventor: John P. Pigott, 5703 Fox Hollow Ct., Sylvania, Ohio 43560

[21] Appl. No.: 649,974

[22] Filed: Feb. 4, 1991

[51] Int. Cl.⁵ .............................................. A61F 2/06
[52] U.S. Cl. ........................................ 623/1; 606/194
[58] Field of Search .................... 623/1, 11, 12, 14; 128/DIG. 25; 604/9; 606/194

[56] References Cited

U.S. PATENT DOCUMENTS

| 4,195,623 | 4/1980 | Zeff et al. ........................... 604/9 |
| 4,195,637 | 4/1980 | Gruntzig et al. . |
| 4,271,839 | 6/1981 | Fogarty et al. . |
| 4,386,601 | 6/1983 | Trich ........................... 128/DIG. 25 |
| 4,508,112 | 4/1985 | Seeler ........................... 128/DIG. 20 |
| 4,577,631 | 3/1986 | Kreamer . |
| 4,649,914 | 3/1987 | Kowalewski ................... 128/207.15 |
| 4,733,665 | 3/1988 | Palmaz . |
| 4,739,762 | 4/1988 | Palmaz . |
| 4,740,207 | 4/1988 | Kreamer . |
| 4,762,130 | 8/1988 | Fogarty et al. . |
| 4,769,029 | 9/1988 | Patel . |
| 4,774,949 | 10/1988 | Fogarty . |
| 4,776,337 | 10/1988 | Palmaz . |
| 4,787,899 | 11/1988 | Lazarus . |
| 4,793,348 | 12/1988 | Palmaz . |
| 4,795,458 | 1/1989 | Regan . |
| 4,877,025 | 10/1989 | Hanson ........................... 128/207.16 |
| 4,955,895 | 9/1990 | Sugiyama et al. ................... 606/191 |

Primary Examiner—David Isabella
Assistant Examiner—Gina Gualtieri
Attorney, Agent, or Firm—Emch, Schaffer, Schaub & Porcello Co.

[57] ABSTRACT

An intraluminal graft includes an inner layer, an intermediate layer and an outer layer defining a passageway for transmisson of blood and a method and apparatus for implantation in a blood vessel.

21 Claims, 8 Drawing Sheets

INTRALUMINAL GRAFT/STENT AND BALLOON CATHETER FOR INSERTION THEREOF

BACKGROUND OF THE INVENTION

The present invention relates to a new and novel intraluminal graft/stent and a method for implantation and is more specifically related to an intraluminal graft/stent particularly well suited for non-invasive treatment of aortic aneurysms and diseased blood vessels.

The treatment of aortic aneurysms usually involves invasive surgery in which the abdominal and/or chest cavity of the patient is opened in order to gain access for treatment of the aorta. One such procedure is described in a book entitled *Surgical Treatment of Aortic Aneurysms* by Denton A. Cooley, M.D., published in 1986 by W. B. Saunders Company.

Additionally, blood vessels can become diseased and the lumen narrowed by atherosclerosis ("hardening of the arteries"). These diseased vessels are presently being opened via numerous angioplastic methods. In order to prevent restenosis, various and currently available stents can be implanted. The present invention is also particularly well-suited to this application.

The device of the present invention will hereinafter be referred to as "intraluminal graft"; however, the breadth of scope of the application should be recognized in that it can be used as a graft to repair aortic or other aneurysms or as a stent in holding open a blood vessel segment which would otherwise have a tendency to become narrowed.

The present invention also relates to a method and a balloon catheter for insertion of such intraluminal graft in a blood vessel.

Treatment of some aneurysms through non-invasive procedures has been known in the art, U.S. Pat. No. 4,740,207 discloses an intraluminal graft specifically designed for non-invasive repairs to damaged blood vessels. It consists of a graft element form of a rolled, generally rectangular section of resilient material suitable for long term residence inside the vessel and expandable substantially uniformly over its entire length from a relaxed small diameter to one or more larger diameters. The graft element is formed with a retaining means extending generally along one of two longitudinal edges. Following positioning in the vessel, the graft element is caused to expand from the smaller diameter to a larger diameter. Such expansion results in the other of the longitudinal edges engaging the retaining means to hold the graft in the expanded position within the vessel. As stated in such patent, the intralumenal graft disclosed therein is particularly well-suited for aneurysm repair by the method disclosed in U.S. Pat. No. 4,577,631.

U.S. Pat. No. 4,577,631 discloses a method and apparatus for repairing aortic aneurysms without surgically invading the abdominal cavity. In the procedure disclosed therein, an occlusion catheter is introduced into a blood vessel down stream of the damaged aorta and fed to a point above the damaged area where it is opened to block the flow of the blood. A tubular prosthetic graft coated with contact adhesive is received about a collapsed balloon catheter which is used to inset the graft into position. The balloon catheter is then expanded to bring the graft into contact with healthy walls of the vessel on either side of the damaged section. Once the graft is permanently adhered to the vessel walls, the two catheters are withdrawn.

U.S. Pat. No. 4,271,839 to Thomas J. Fogarty et al., discloses a balloon catheter and method for dilating a partially occluded section of a blood vessel and includes balloon means inverted within the catheter and having a mouth peripherally sealed to the distal end. The balloon is evertable out of the catheter in response to the exertion of fluid pressure within the catheter and laterally expansible in response to continued exertion of internal fluid pressure to dilate the occlusion.

U.S. Pat. No. 4,776,337 to Julio C. Palmaz discloses an expandable intraluminal graft and method and apparatus for implanting within a body passageway such as a blood vessel. The apparatus comprises a catheter having an expansible balloon and means for mounting and retaining the graft during insertion in the body.

U.S. Pat. No. 4,762,132 discloses a catheter having a helical balloon attached to its distal end which serves, when inflated as a therapeutic tool for removal of blood clots.

U.S. Pat. No. 4,195,637 discloses a catheter having a flexible dilation element comprising a cylindrical foldable wall and two lumens, one for dilating the flexible dilating element and the other for infeeding blood or a contrast agent into the blood vessel.

The disclosures of the above patents are incorporated herein by reference and copies are herewith enclosed.

SUMMARY OF THE INVENTION

The intraluminal graft/stent of the present invention includes inner and outer layers of resilient material suitable for implantation in a blood vessel. Each of the inner and outer layers defines an annular cross-sectional configuration. The inner and outer layers are joined together at their opposite ends and, when expanded cooperate to define a cavity between the layers for receiving a reinforcing layer of plastic material and a tubular passageway defined by the inner surface of the inner layer for directing the flow of blood.

Preferably the ends of the outer layer are ballooned outwardly and, thus have a slightly larger diameter than the central portion in order to assist such ends in becoming firmly engaged with the interior wall portions of the blood vessel.

Means are provided for introducing a plastic material into the cavity between the inner and outer layers following implantation of the inner and outer layers into the damaged area of the blood vessel where the outer layer is grafted into contact with healthy walls of the vessel on opposite sides of the damaged section. The means for introducing plastic material include inlet and outlet valves. Inflow and outflow tubes, each mounted on the end of a catheter, are connected to the respective inlet and outlet valves. The catheters with the inflow and outflow tubes engaged to the inlet and outlet valves, respectively, are inserted into a remote vessel, preferably the femoral artery, and directed to the desired repair site. Air is then introduced through the inflow tube to expand the outer layer, separating it from the inner layer, and causing the ends of the outer layer to engage the interior wall portions of the vessel. Following engagement of the outer layer to the interior surface of the vessel, plastic material is introduced into the cavity. The outflow tube may be connected to a pressure monitor which permits venting of air from the cavity as plastic is introduced therein and assists in confirming that the cavity between the inner and outer layers becomes completely filled with plastic.

Additionally, a new and improved balloon catheter is provided for insertion of the intraluminal graft to the desired site for repair of the blood vessel. Such balloon catheter is provided with one or more longitudinal passageways which permit the flow of blood through the blood vessel even though the balloon catheter is expanded in the blood vessel.

DETAILED DESCRIPTION OF THE INVENTION

Figure 1:
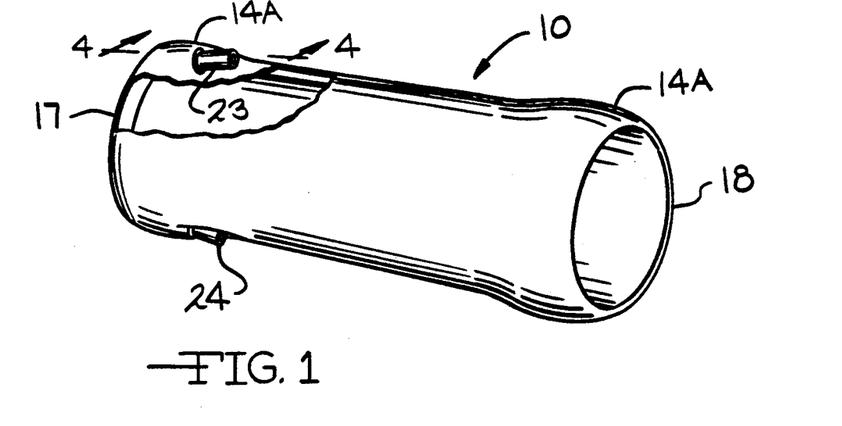
FIG. 1 is a perspective view of the intraluminal graft of the present invention with a portion broken away and showing valves communicating with the space between the inner and outer layers.

Referring now to the drawings, the intraluminal graft 10 of the present invention includes spaced apart inner and outer tubes 12 and 14 respectively formed of a flexible, semi-rigid material suitable for insertion in a blood vessel for long periods of time. These materials are well-known in the art and include ones manufactured of Dacron ® and Gore-Tex ®(polytetrafluoroethylene). The inner surface of the inner tube 12 defines a blood flow passageway P. Preferably, such inner surface is coated with a material such as expanded polytetrafluoroethylene (ePTFE) which is an accepted vascular conduit. The inner tube 12 is smaller than the outer tube 14 so that there will be a space or chamber 16 between the inner tube 12 and outer tube 14 when they are in their expanded condition. The diameter of the inner tube 12 will range between 4 and 30 mm. while the diameter of the outer tube 14 will range between 6 and 34 mm. when implanted. In the central area of the graft 10 expanded to span the damaged portion of the blood vessel, the space between the inner tube 12 and outer tube 14 should be on the order of ½ to 3 mm.

The intraluminal graft 10 extends from a proximal end 17 to a distal end 18 with a seal 15 being provided between the inner tube 12 and the outer tube 14 near each of such ends 17 and 18. A suitable method such as heat sealing may be used for the seal 15. The distance between such ends 17 and 18 and, therefore, the length of the graft 10 used in any repair procedure is determined by the size of the patient and condition of the vessel being repaired. Prior to implantation, the size of the blood vessel and length of the damaged section to be repaired will be determined by CT, MRI scan, ultrasound or angiography in order to determine the proper length and size for the graft 10 which is to be used on that patient.

In the preferred embodiment, the portion of the outer tube 14 adjacent the proximal end 17 and distal end 18 is ballooned outwardly as at 14A to a slightly larger diameter than the main portion of the outer tube 14. This will assist in providing a firm engagement between the ballooned portions 14A of the outer tube 14 and the inner wall of the blood vessel. The ends of the outer tube 14 may be folded inwardly as shown in FIGS. 4–7 in order to provide a smooth seal 15.

The outer tube 14 is provided with an inflow aperture 22, to which is attached an inflow valve 23, and an outflow aperture (not shown) to which is attached an outflow valve 24. The inflow valve 23 provides means for introducing both pressurized air and subsequently plastic material into the chamber 16 between the inner tube 12 and outer tube 14. The outflow valve 24 provides means through which air may be evacuated from the chamber 16 while the plastic is being introduced therein. The outflow valve 24 may be identical to the inflow valve 23; accordingly, only the inflow valve will be described.

Figure 2:
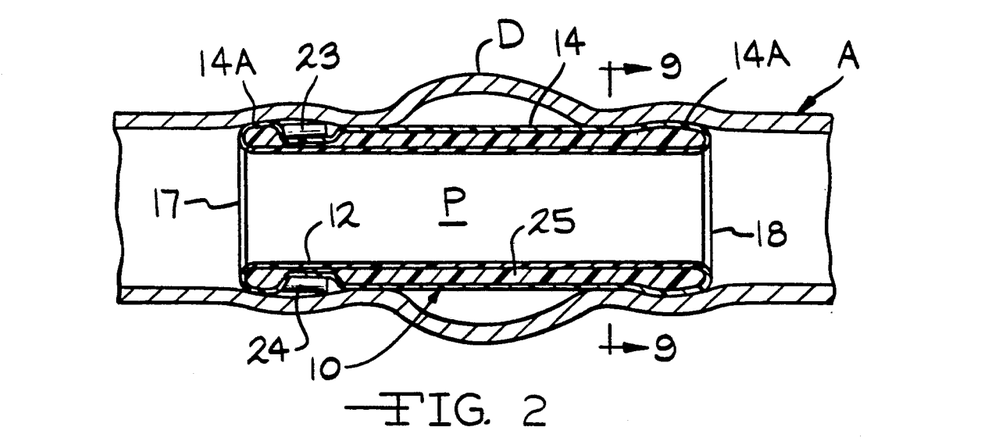
FIG. 2 is a longitudinal sectional view showing the intraluminal graft implanted in a blood vessel.

Referring now to FIG. 2, there is shown the intraluminal graft 10 of the present invention is completed form following implantation in a damaged or diseased aorta or other blood vessel A. As can be seen, the graft 10 is positioned with the proximal end 17 on one side of the damaged section D of the blood vessel A and the distal end 18 on the other side. The outer surface of the ballooned portions 14A sealingly engaged to healthy tissue on the inner surface of the blood vessel A. As can be seen, the inflow valve 23 and outflow valve 24 remain in the blood vessel A following implantation. As can also be seen, the chamber 16 between the inner tube 12 and outer tube 14 has been filled with plastic material such as an acrylic to form an interior reinforcing layer 25 having good strength and rigidity for long term residence within the body. The inner surface of the inner tube 12, preferably coated with a good conductor for blood, defines a passageway P directing the flow of blood. The seals between the ballooned portions 14A adjacent the distal end 17 and proximal end 18 and the inner wall of the blood vessel A prevent seepage of blood to the damaged section D.

Referring now to FIGS. 4-8, the inflow valve 23 includes a tubular housing 26 which is open at one end and has a flange 27 at the other end adhesively or otherwise permanently secured to the outer tube 14 in an area encircling the inflow aperture 22. The tubular housing 26 supports an interior wall 28 having a cone-shaped central area 29 with an aperture 30 formed therein.

Retained against the proximal side of the interior wall 28 is a one-way valve 32 formed of rubber or other sealingly resilient material. The one-way valve 32 includes a flange 33, a tubular housing 34 extending away from said flange 33 and terminating in a pair of lips 35. The lips 35 are normally in sealing engagement with one another but may readily be opened by the insertion of a device inserted into the chamber defined by the flange 33 and housing 34. Even in the absence of a device to separate lips 35, it is possible for pressurized air or other fluid flowing through the chamber defined by the flange 33 and tubular housing 34 to be expelled through the aperture defined by the lips 35. However, in the absence of some device prying the lips 35 open, it is not possible for any such fluid to move in the reverse direction through such aperture. Thus, the valve 32 functions effectively as a one-way valve permitting the flow of fluid therethrough and into the chamber 16 but preventing the outflow from such chamber unless a device is inserted to open the lips 35 and permit such outflow. The lips 35 may be joined together at their respective ends if it desired to hold them more snugly in sealing engagement with each other.

The one-way valve 32 is retained in the tubular housing 26 by means of a retaining ring 36 clamping the flange 33 against the proximal side of the interior wall 28. The distal end of the tubular housing 26 is provided with a cap 37 having a flange sealingly retained to the inner wall. The cap 37 has an opening 38 for receiving a catheter and other members of the inflow system for directing the graft 10 in collapsed and unfilled condition to the site of implantation and for introducing air and thereafter plastic into the chamber 16.

Figure 3:
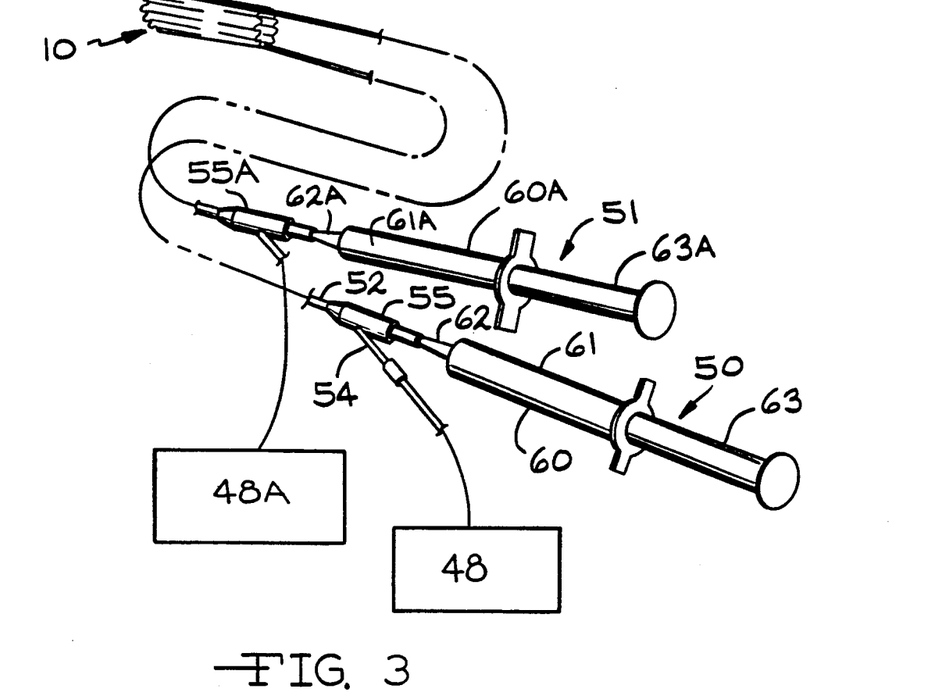
FIG. 3 is a schematic view showing apparatus for implanting the intraluminal graft.
Figure 4:
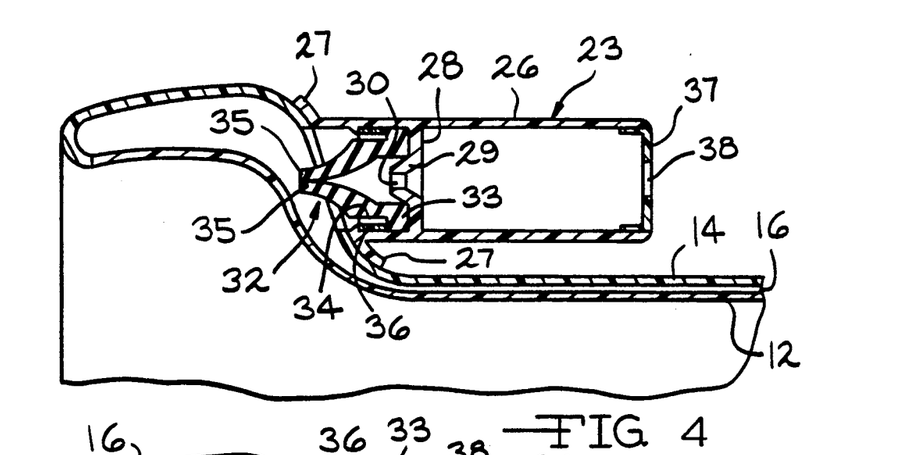
FIG. 4 is a sectional view taken through line 4—4 of FIG. 1 showing one of the valves for introducing air and subsequently plastic between the layers.

Referring now to FIG. 3, there is illustrated schematically an infeed system 50 connected to the inflow valve 23 and an outflow system 51 connected to the outflow valve 24 of the intraluminal graft 10. The infeed system 50 and outflow system 51 cooperate to direct the intraluminal graft 10 in collapsed and unfilled condition through a remote vessel, preferably through the femoral artery to the site of the blood vessel A to be repaired. The inflow system 50 and outflow system 51 cooperate to act as a catheter in inserting and guiding the intraluminal graft 10 through such femoral artery to the damaged blood vessel A. As shown schematically in FIG. 3 and in more detail in FIGS. 5, 6 and 8, the infeed system includes a hollow guidewire 52 having a central passageway 53 a flexible tube 54 encircling such guidewire in spaced relationship thereto and a balloon support 38.

The balloon support 38 encircles the flexible tube 54 and has its end portions 39 adhesively or otherwise sealingly engaged thereto. The flexible tube 54 has an aperture 40 in an area aligned with that portion of the balloon support 38 between the sealingly engaged end portions 39. The hollow guidewire 52 terminates in an outwardly directed segment 58 which extends through the aperture 40 of the flexible tube 54 in sealing engagement therewith. The flexible tube 54 has a passageway 56 through which air and subsequently plastic material may be introduced into the chamber 16.

The hollow wire 52 is connected to a source of pressurized air which is utilized to expand the balloon support 38 in the are of the tubular housing 26 between the interior wall 28 and the cap 37. Such expansion of the balloon support 38 functions to fix in place the flexible tube 43 and the hollow guidewire 52 with the flexible tube 54 extending between the lips of the one-way valve 32 35 and into the chamber 16 (See FIGS. 5 and 6).

For example, the hollow guidewire 52 may be attached to a syringe 60 having a barrel 61 from which a nozzle 62 extends. The nozzle 62 is engaged to a coupling 55 at the end of the hollow guidewire 52. A plunger 63 is slidingly engaged within the housing for expelling air from the housing 61 through the nozzle 62 and the passageway 53 to expand the balloon support 38 when positioned as hereinafter described. The flexible tube 54 is attached to a combination monitor 48, air supply and plastic supply.

Figure 5:
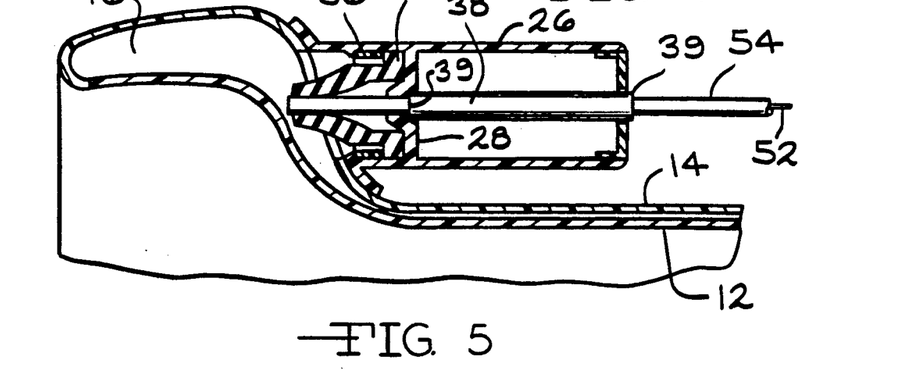
FIG. 5 is a view similar to FIG. 4 showing a combined catheter and air and plastic feeder mechanism inserted into the valve.

The procedure for inserting the intraluminal graft 10 will be described in relation to FIGS. 3-8. The intraluminal graft 10 is initially collapsed to a size permitting its insertion via the femoral artery. The infeed system 50 is then affixed to the inflow valve 23 by inserting the proximal end of the flexible tube 54 through the opening 38 of the cap 37 and through the aperture 30 of the cone-shaped central area 29 of the interior wall 28 until it protrudes between the lips 35 of the one-way valve 32 as shown in FIG. 5. Thus, the flexible tube 54 is ready to introduce fluid into the chamber 16 between the inner tube 12 and outer tube 14. When in such position, the balloon support 38 is positioned in the tubular housing 26 and extends from the interior wall 28 to the cap 37. As previously mentioned, the proximal end of the hollow guidewire 52 which bends outwardly through the aperture 40 of the flexible tube 54 is aligned with the interior of the balloon support 38. With the balloon support 38 so positioned, air is injected into the passageway 53 by depressing the plunger 63 of the syringe 60 to expand such balloon support 38 firmly against the walls of the tubular housing portion 26, the interior wall 28 and the cap 37 thus providing a solid connection between the flexible tube 54 and the valve 23.

As will be appreciated from FIG. 3, the outflow system 51 is similar in that there is also provided a syringe 60A having a barrel 61A from which extends a nozzle 62A. A plunger 63A is slidingly engaged within the housing 61A. The nozzle 62A is detachably secured to a coupling 55A for introducing pressurized air into the hollow guidewire 52A. The outflow system 51 also includes a flexible tube 54A encircling the hollow guidewire 52A.

Prior to insertion of the intraluminal graft 10 into the body, the outflow system 51 is fastened to the outflow valve 24 in a manner similar to the fastening of the inflow system 50 to the inflow valve 23. Air is introduced through the hollow guidewire 52 to expand the balloon support within the outflow valve 24 thus providing a solid connection between the flexible tube 54A and the outflow valve 24.

The intraluminal graft 10 in collapsed condition and carried on the respective inflow system 50 and outflow system 51 is now ready to insertion through the femoral artery and into alignment with the damaged portion of the blood vessel. The graft 10 is positioned so that the respective enlarged ends 14A are aligned with healthy portions of the blood vessel A with the central portion of the graft 10 spanning the damaged portion D of the blood vessel.

When so positioned, pressurized air or other fluid is introduced through the passageway 56 of the flexible tube 54 into the chamber 16 between the inner tube 12 and the outer tube 14 to expand the intraluminal graft 10, separating the inner tube 12 and outer tube 14 from each other and forcing the enlarged ends 14A into sealing engagement with the interior wall of the blood vessel. This is the position of the respective members shown in FIG. 6. The second monitor 48A is in a closed position at this time to prevent the escape of air from such chamber 16.

Figure 6:
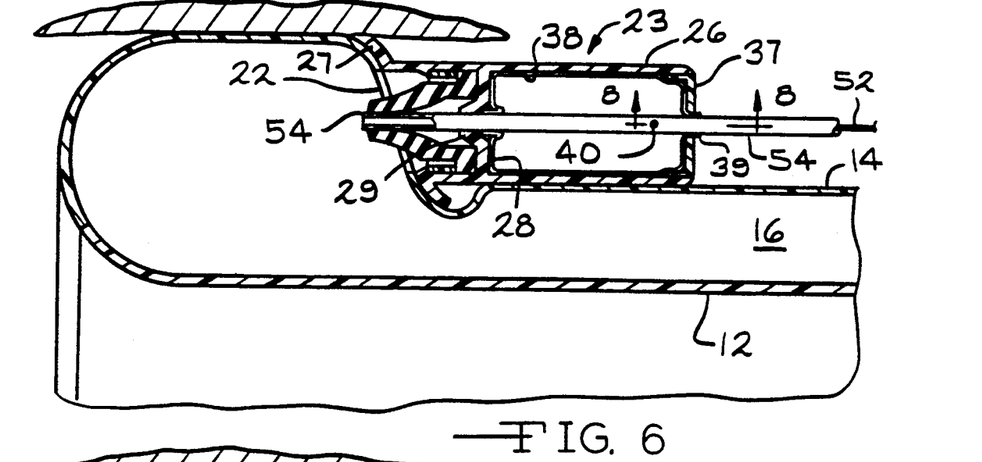
FIG. 6 is a view similar to FIG. 5 showing relative positioning of the members after introduction of pressured air through the valve into the space between the inner and outer layers.

With the intraluminal graft 10 so positioned, plastic material is then introduced by the monitor 48 into the passageway 56 of the flexible tube 54, out of the proximal end of such passageway 56 and into the chamber 16. During the introduction of such plastic material into the chamber 16, the other monitor 48A is activated to permit the evacuation of air from the chamber 16 at substantially the same rate as the plastic is being introduced. When the chamber is filled with plastic material, the monitor 48A will sense that fact and relay information to the physician or, if desired automatically to the pressure monitor 48 and the inflow of plastic material will then be stopped.

Figure 7:
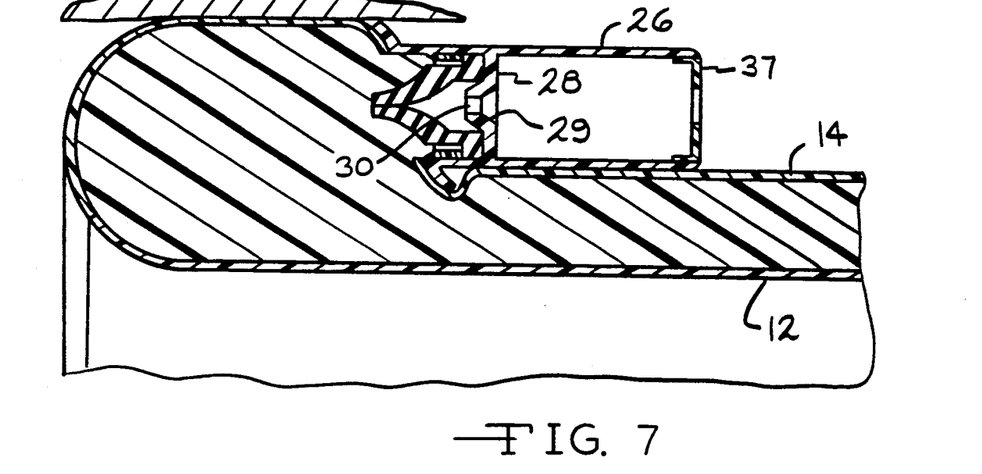
FIG. 7 is a view similar to FIG. 6 following the introduction of plastic between the inner and outer layers.
Figure 8:
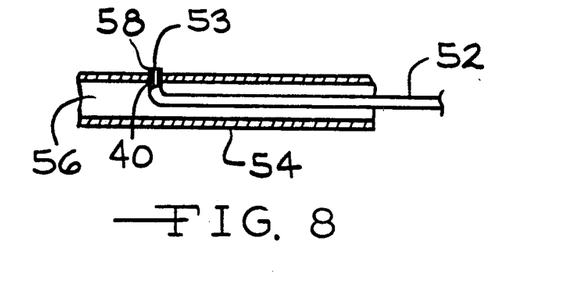
FIG. 8 is a sectional view taken through line 8—8 of FIG. 6.

Following completion of the step of introducing plastic into the chamber 16, the plungers 63 and 63A are released to release air pressure from the respective balloon supports 38. Thereafter, the flexible tubes 54 and hollow guidewires 52 will be withdrawn carrying with them the balloon supports 38 but leaving in place all members of the intraluminal graft 10 including the inflow valve 23 and outflow valve 24. Since the inflow valve 23 and the outflow valve 24 are each provided with one-way valves 32, there is no possibility for the plastic material to escape from the chamber 16 following withdrawal of the respective inflow system 50 and outflow system 51 from the valves 23 and 24.

Figure 9:
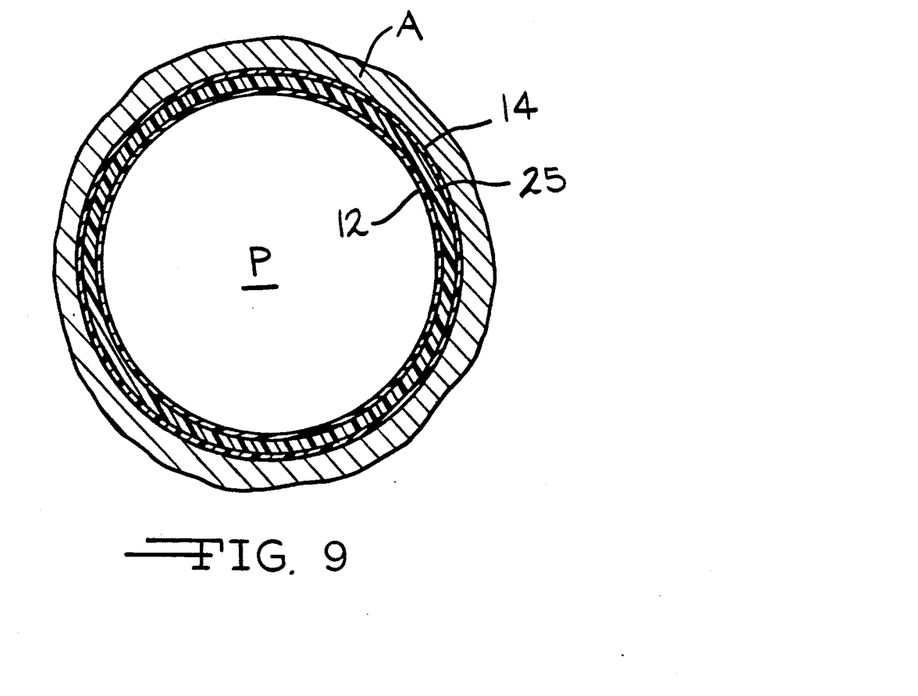
FIG. 9 is a sectional view taken through line 9—9 of FIG. 2.

As can be clearly seen in FIG. 2 and FIG. 9, the intraluminal graft 10 is firmly engaged in blood vessel A with the enlarged ends 14A of the outer tube 14 providing the primary areas of sealing contact with the inner wall portions of the blood vessel A.

Referring now to FIGS. 10-14, there is shown a modified embodiment and a modified method for implanting the intraluminal graft into the damaged blood vessel. In this embodiment there is provided an intraluminal graft 70 having an inner tube 72 and an outer tube 74 which are spaced apart to define a chamber 76. The inner tube 72 may be fastened to the outer tube 74 by a distal end member 77 and a proximal end member 78. Under this embodiment the inflow valve 23 and outflow valve 24 are attached to the proximal end wall 78.

Figure 10:
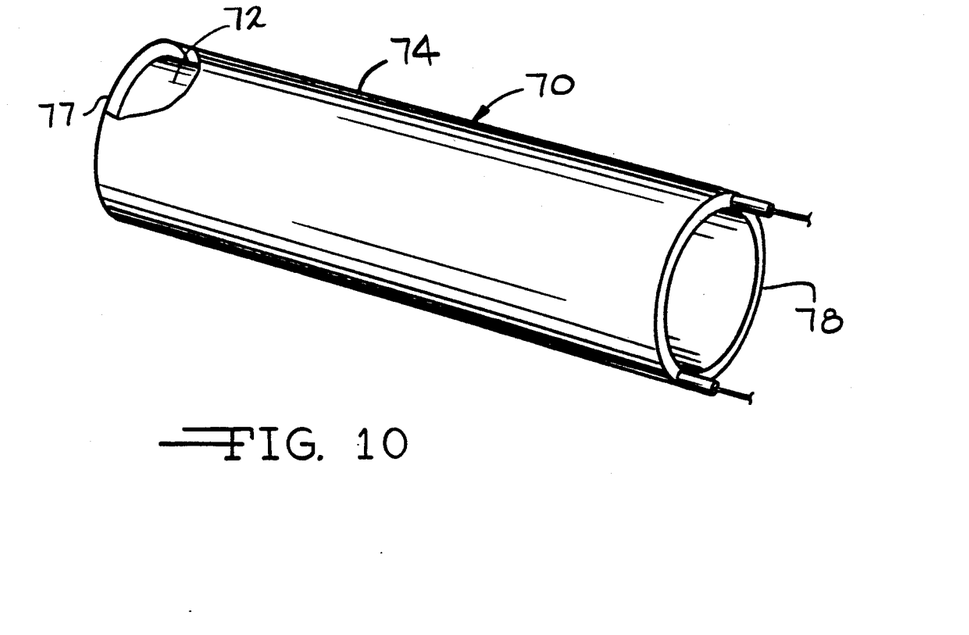
FIG. 10 is a perspective view showing a modified embodiment with inflow and outflow tubes attached thereto.

An inflow line 84 is attached to the inflow valve 23 and an outflow line 86 is attached to the outflow valve 24. The inflow line 84 and outflow line 86 may include a hollow guidewire, flexible tube and balloon support (not shown) similar to that previously described for introducing air to inflate the balloon support and later for introducing air into the chamber and then for introducing plastic while venting the air. Other types of valves and connecting mechanisms may be utilized without departing from the scope of the present invention.

Figure 11:
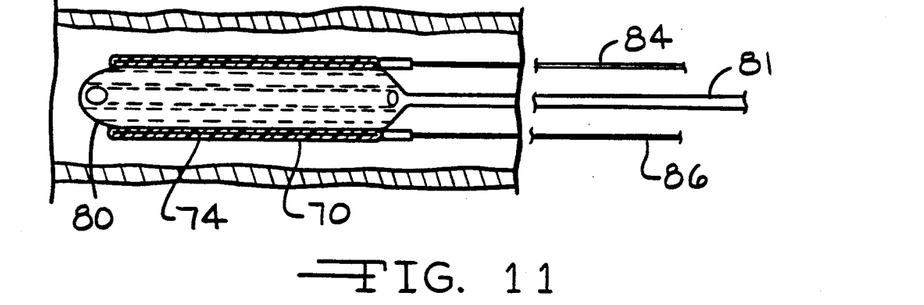
FIG. 11 is a longitudinal sectional view showing the modified intraluminal graft in collapsed condition positioned over a schematically illustrated balloon catheter of the present invention during insertion in a remote artery for feeding to the damaged section of the blood vessel.
Figure 12:
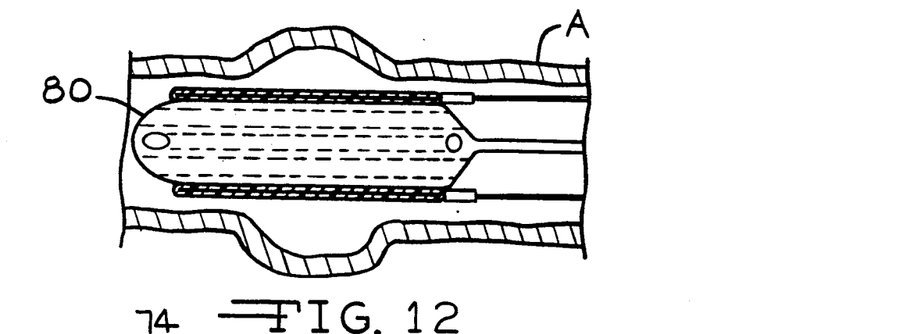
FIG. 12 is a view similar to FIG. 11 showing the catheter and collapsed graft at the site of the damaged vessel with the catheter expanded.
Figure 13:
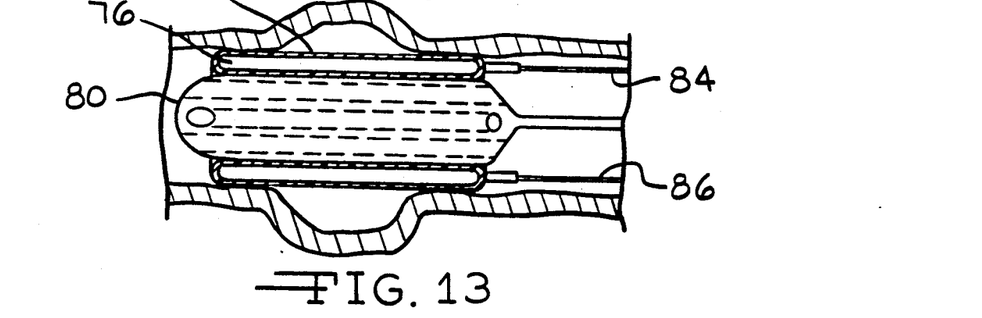
FIG. 13 is a view similar to FIG. 12 after the introduction of air into the space between the inner and outer layers.

As can be seen in FIGS. 11-13 under this embodiment a balloon catheter 80 is utilized to direct the intraluminal graft 70 into the femoral artery and through the blood vessels to the damaged portion of the blood vessel. The balloon catheter 80 may have a series of longitudinal passageways 82 which permit the flow of blood therethrough while the catheter is being inserted, thereby preventing total vessel occlusion and providing a continuous measure of blood flow through the vessel. The catheter 80 free end portion is mounted on the end of a tube 81 through which pressurized air may be introduced. Wire guide means (not shown) may be utilized to assist in guiding the catheter 80 to the damaged or diseased vessel.

After reaching the site of the damaged blood vessel A to be repaired, pressurized air is introduced through the tube 81 to expand the balloon catheter 80 as shown in FIG. 12. As will be appreciated, the radial extent to which the balloon catheter 80 may be expanded will be limited by the size of the inner tube 12.

Figure 14:
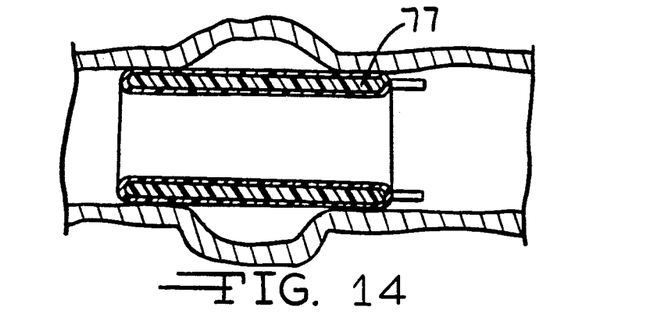
FIG. 14 is a view similar to FIG. 13 showing the modified intraluminal graft fully implanted.

Simultaneously with or after expansion of the balloon cather, pressurized air is introduced through inflow line 84 and into the chamber to expand the outer layer 74 into engagement with the interior wall portions of the blood vessel on opposite sides of the damaged area. This is the position shown in FIG. 13. As in the previous embodiment during this step, the valve connected to the outlet line 86 is in a closed position to retain air in the chamber 76. Thereafter, plastic material is introduced into the inflow line 84 to fill the cavity 76 forming the reinforcing layer 87 as shown in FIG. 14. During introduction of such plastic material through the inflow line 84, the air entrapped in the cavity 76 is permitted to vent through the outflow line 86. Following such introduction of plastic material, the air to the catheter 80 is vented, permitting the catheter to be reduced in diameter and withdrawn from the implanted intraluminal graft 70. The inflow line 84 and outflow line 86 are similarly withdrawn from their respective inflow valves 23 and outflow valves 24 as in the previous embodiment.

Figures 15, 16:
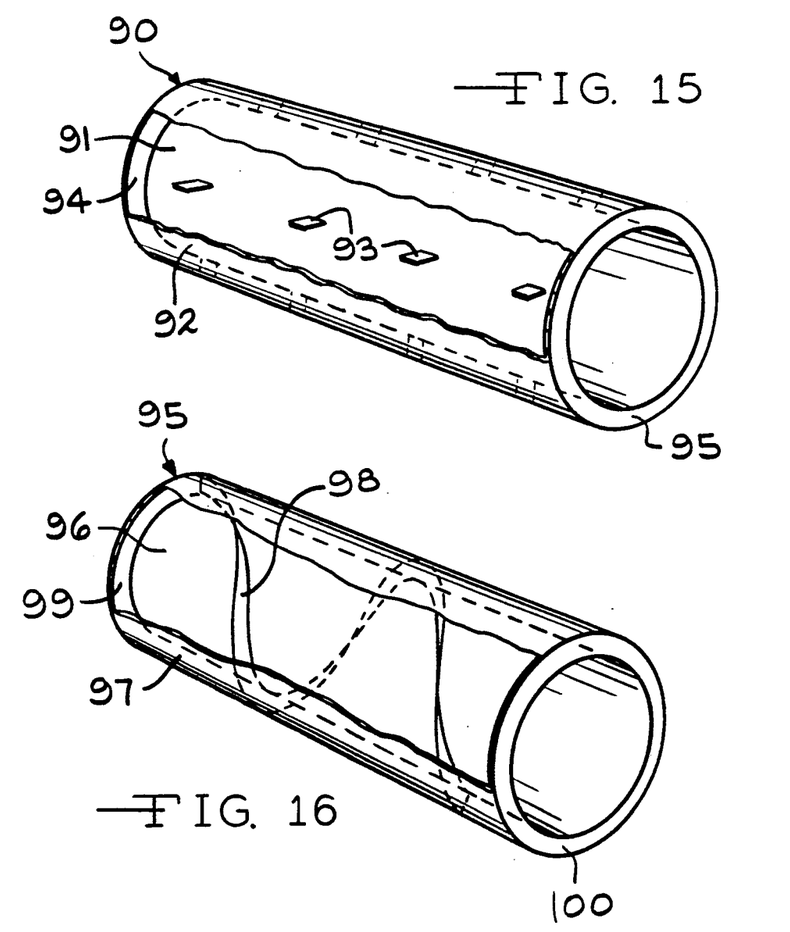
FIGS. 15 and 16 are perspective views, partly in section, of further modified intraluminal grafts.

Referring now to FIGS. 15 and 16, there are shown modified intraluminal grafts. In FIG. 15 there is shown an intraluminal graft 90 having an inner tube 91 and an outer tube 92 maintained in spaced relationship thereto and having a plurality of reinforcing tabs 93 joining the inner tube 91 to the outer tube 92. These tabs provide reinforcing while permitting the introduction of air and later of plastic material into the cavity between the inner and outer tubes 91 and 92 respectively. The inner and outer tubes are sealed together by end members 94 and 95. Valve means (not shown) are provided for the introduction of air and plastic and for the venting of air during the introduction of plastic.

In FIG. 16 there is provided a graft 96 having an inner tube 96 and an outer tube 97 with a spiral reinforcing member 98 joined to the inner tube and the outer tube 97. The inner and outer tubes are sealed together by end members 99 and 100.

Figure 17:
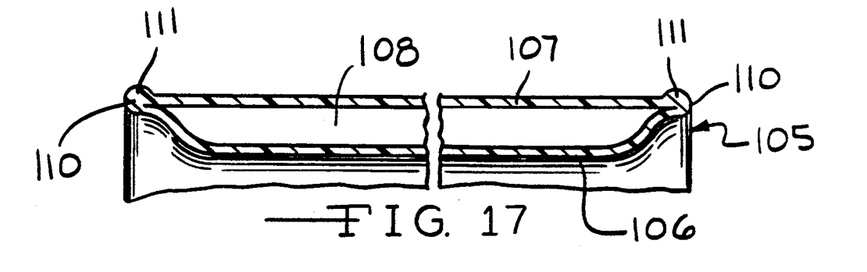
FIG. 17 is a fragmentary sectional view of yet another embodiment.

Referring to FIG. 17, there is shown yet another embodiment in which an intraluminal graft 105 includes an inner tube 106, an outer tube 107 joined together to form a chamber 108 for receiving the plastic reinforcement. Under this embodiment, there is formed a seal 110 between the inner and outer tubes 106 and 107 which extends radially outwardly to provide a raised lip 111 for engaging the inner wall of the vessel being repaired.

The procedure for implanting the intraluminal graft 10 of the present invention includes initially determining the proper size of inner tube 12 and outer tube 14 to be utilized by available scanning methods. Thus, the size of the outer surface of the outer tube 14 should be slightly larger when expanded to its full diameter than the size of the interior wall of the portions of the blood vessel to which the proximal end 17 and distal end 18, respectively, are to be attached. Thus, the proximal end 17 and the distal end 18 will desirably become attached to portions of the blood vessel which are not diseased with the intermediate portions spanning the diseased portion of the blood vessel to be repaired.

Referring now to FIGS. 18–21 there is provided a balloon catheter 180 for delivering the intraluminal graft to the desired repair site of the blood vessel while permitting blood to flow through such blood vessel even when in the expanded condition.

The catheter 180 includes a semi-rigid tube 181 having sufficient flexibility to be fed through a series of blood vessels but sufficient rigidity that it will not deform as a result of pressurized fluid acting against it. The tube 181 has a central passageway 182 extending a distal end 183 which may be utilized to inject die or other fluids into the blood. If desired and if it is not necessary to inject fluids into the blood, the distal end 183 could be closed.

Secured to the distal end 183 of the tube 181 by means of a seal 184 is a second semi-rigid tube 185 spaced from the tube 181 and cooperating therewith to define an annular chamber 186. The second tube 186 has an aperture 187.

A balloon 190 has spaced apart distal and proximal ends 191 and 192, respectively, which are sealed to the second tube 185 on opposite sides of the aperture 187 by means of adhesive 193. The balloon 190 includes an outer annular wall 195 extending from the distal end 191 to the proximal end 192 and a plurality of longitudinally extending flexible tubes 196 defining passageways 197 and terminating at opposite ends at the outer annular wall 195. Thus, when the balloon is in the expanded condition shown in FIGS. 20 and 21, blood may flow through the passageways 197 thereby permitting continuous flow of blood through the blood vessel even through the balloon catheter is expanded therein.

Figures 18, 19:
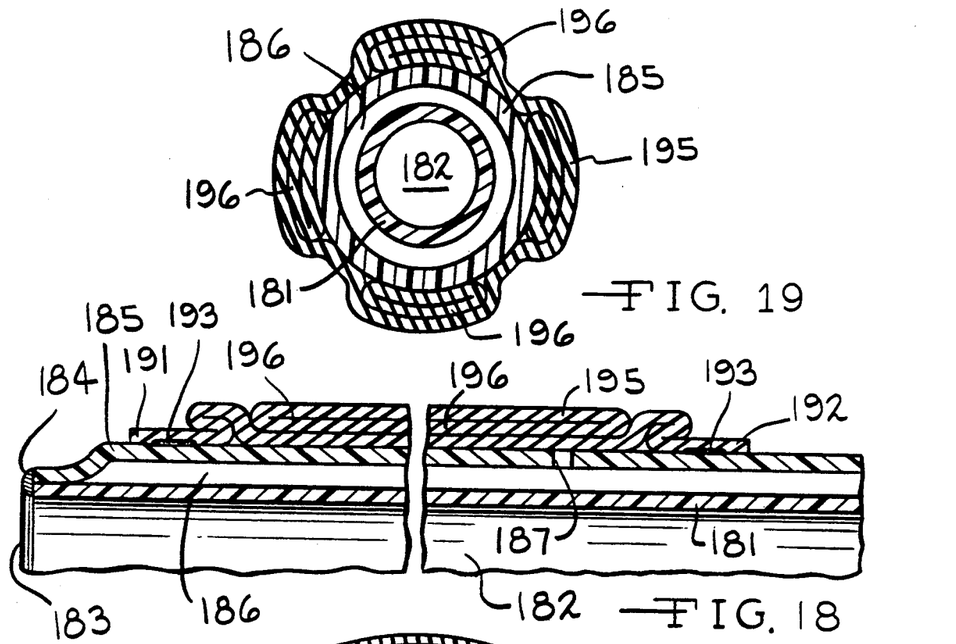
FIG. 18 is a fragmentary view in longitudinal section of the balloon catheter of the present invention in the collapsed condition.
FIG. 19 is a cross-sectional view of such catheter with the balloon portion in the collapsed condition.
Figure 20:
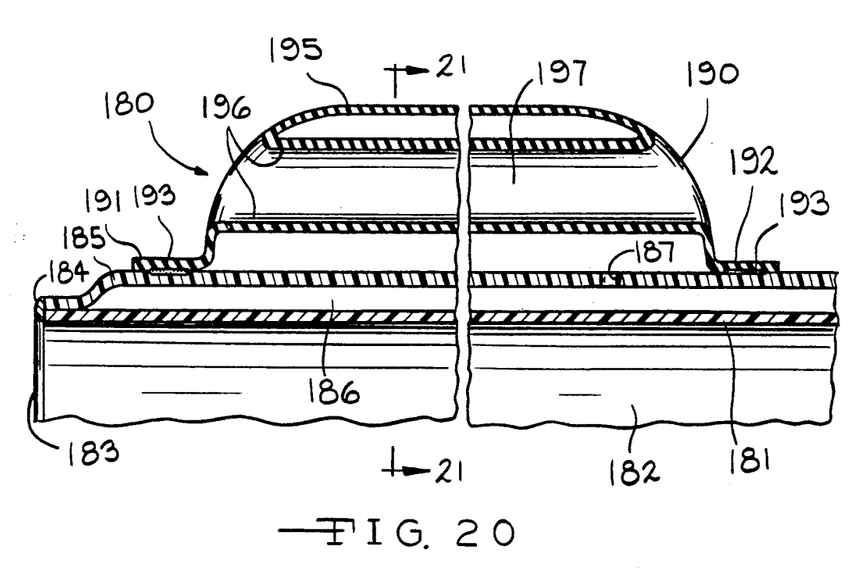
FIG. 20 is a view similar to FIG. 18 showing the balloon in the fully expanded position.
Figure 21:
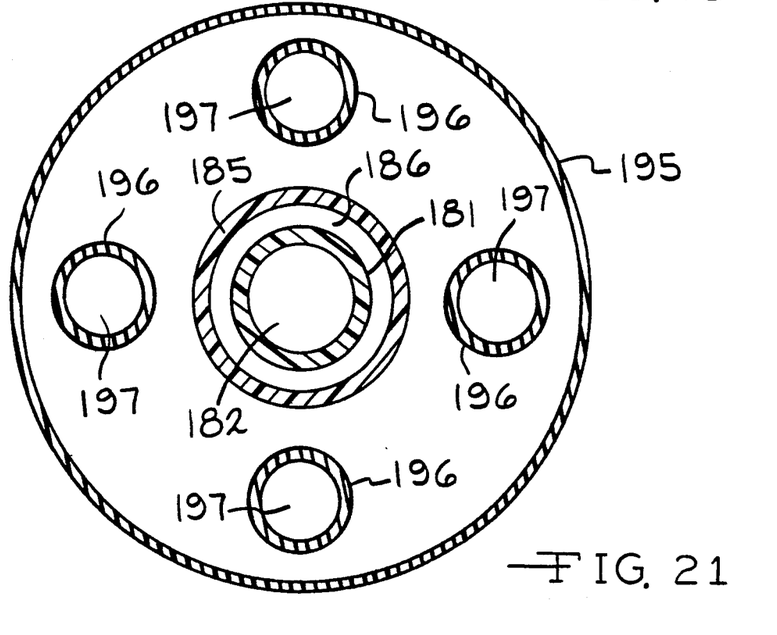
FIG. 21 is a view similar to FIG. 19 showing the balloon in the fully expanded position.

As will be appreciated, the catheter 180 will be in the collapsed condition shown in FIGS. 18 and 19 during the process of inserting it in the blood vessel, carrying thereon the intraluminal graft. When it reaches the site of the damaged vessel requiring repair, pressurized air or other fluid may be introduced into the annular chamber 186 and through the aperture 187 to expand the balloon 190 to the position shown in FIGS. 20 and 21.

If the catheter 190 is used to implant an intraluminal graft of the types disclosed in the present application, the introduction of pressurized air to expand the balloon will be performed prior to or simultaneously with the introduction of air into the intraluminal graft.

The present invention permits repair of diseased aorta and other blood vessels using simple, non-invasive procedures while at the same time providing a repair means which is superior to those utilized heretofore.

I claim:

1. An intraluminal graft member for positioning in a blood vessel having an inner wall surface comprising inner and outer layers of resilient material suitable for implantation in said blood vessel, each of said inner and outer layers defining an annular cross-sectional configuration and which, when in a fully expanded position, the outer layer encircles the inner layer in spaced relationship forming a chamber therebetween, said chamber extending longitudinally from a proximal end to a distal end, means in the vicinity of each of said proximal and distal ends for joining said inner layer to said outer layer, valve means for introducing fluid into said chamber, said inner and outer layer being collapsible in the absence of fluid in said chamber to a size permitting introduction thereof, including said valve means, into said blood vessel wherein said outer layer engages said inner wall surface of said blood vessel, and means for sealing said valve means following introduction of fluid into said chamber, said inner layer forming a passageway for the flow of blood therethrough following introduction of fluid into said chamber.

2. An intraluminal graft member according to claim 1 further including an outflow aperture for venting said chamber and means for sealing said outflow aperture.

3. An intraluminal graft member according to claim 1, wherein at least one of the proximal end and the distal end of said outer layer has a larger cross-sectional size that other portions of said outer layer.

4. An intraluminal graft member according to claim 1, wherein said means for sealing said inflow aperture comprises a one-way valve having a pair of lip members defining an outlet end extending into said chamber and having an inlet end outside of said chamber, the outlet end of said lip members, in normal position, being resiliently urged into sealing engagement with each other and being moveable to a spaced apart position by the application of pressure only from said inlet end.

5. An intraluminal graft member comprising inner and outer layers of resilient material suitable for implantation in a blood vessel, each of said inner and outer layers defining an annular cross-sectional configuration and which when in a fully expanded position, the outer layer encircles the inner layer in spaced relationship forming a chamber therebetween, said chamber extending longitudinally from a proximal end to a distal end, means in the vicinity of each of said proximal and distal ends joining together said inner and outer layers, an inflow aperture for introducing fluid into said chamber, and means for sealing said inflow aperture, said means for sealing said inflow aperture comprising a one-way valve having a pair of lip members defining an outlet end extending into said chamber and having an inlet end outside of said chamber, the outlet end of said lip members, in normal position, being resiliently urged into sealing engagement with each other and being moveable to a spaced apart position by the application of pressure only from said inlet end and means for mounting on a catheter, said mounting means comprising a housing having (a) a side wall, (b) an interior wall and (c) an end wall defining a chamber, said side wall extending beyond said interior wall to an open end engaged to said outer layer, means for engaging said valve to said interior wall and the portion of said side wall extending beyond said interior wall, each of said interior wall and said end wall having an aperture, a catheter extending through said valve to a position between said lip members, said catheter having an inflatable bladder positioned in said housing having a first end sealingly engaged to said catheter in the vicinity of said end wall and a second end sealingly engaged to said catheter in the vicinity of said interior wall, said bladder, when inflated, firmly engaging said housing.

6. An intraluminal graft member according to claim 1 further including means intermediate said proximal and distal ends connecting said inner and outer layers.

7. An intraluminal graft member according to claim 6, wherein said intermediate connecting means comprises a plurality of tabs extending between said inner and outer layers.

8. An intraluminal graft member according to claim 6, wherein said intermediate connecting means comprises a continuous web extending along a substantially helical path.

9. An intraluminal graft for implantation in a blood vessel comprising inner and outer layers of resilient material, each of said inner and outer layers defining a tubular segment having an annular cross-sectional configuration, said outer layer encircling the inner layer in spaced relationship forming a chamber therebetween, said chamber extending longitudinally from a proximal end to a distal end, said chamber having a material therein for (a) maintaining said outer layer spaced from said inner layer and (b) maintaining said inner layer open to define a passageway for transmission of blood, said outer layer being of a size suitable for engaging the interior wall of a blood vessel and valve means communicating with said chamber for introducing said material into said chamber.

10. An intraluminal graft member according to claim 9 further including inflow means for introducing said intermediate layer into the space between said inner and outer layers after said inner and outer layers are positioned in a blood vessel.

11. An intraluminal graft according to claim 10 further including outflow means for monitoring the inflow of said intermediate layer.

12. An intraluminal graft member according to claim 9, wherein said outer layer includes a proximal end portion and a distal end portion, at least one of which has a larger cross-sectional size than other portions of said outer layer.

13. An intraluminal graft member according to claim 9 further including means extending through said intermediate layer connecting said inner and outer layers.

14. An intraluminal graft member according to claim 13, wherein said connecting means comprises a plurality of tabs extending between said inner and outer layers.

15. An intraluminal graft member according to claim 13, wherein said connecting means comprises a continuous web extending along a substantially helical path.

16. An intraluminal graft suitable for implantation in a blood vessel comprising inner, intermediate and outer layers of resilient material joined together, defining a tubular segment having an annular cross-sectional configuration, said inner layer defining a passageway for transmission of blood, and cooperating with said outer layer to define a chamber containing said intermediate layer, said graft extending longitudinally from a proximal end to a distal end and having means on said outer layer at each of said proximal and distal ends engageable with said blood vessel, and valve means communicating with said chamber for introducing said intermediate layer therein.

17. An intraluminal graft member according to claim 16, wherein said valve means is located in the vicinity of one of said proximal end and said distal end.

18. An intraluminal graft member according to claim 16, wherein said outer layer has a larger cross-sectional size at one said proximal end and said distal end than other portions of said outer layer.

19. An intraluminal graft member according to claim 16 further including reinforcing means extending through said intermediate layer and joined to said inner and outer layers.

20. An intraluminal graft member according to claim 19, wherein said reinforcing means comprises a plurality of tabs.

21. An intraluminal graft member according to claim 19, wherein said reinforcing means comprises a continuous web extending along a substantially helical path.

* * * * *

UNITED STATES PATENT AND TRADEMARK OFFICE
CERTIFICATE OF CORRECTION

PATENT NO. : 5,156,620

DATED : Oct. 20, 1992

INVENTOR(S) : John P. Pigott

It is certified that error appears in the above—identified patent and that said Letters Patent is hereby corrected as shown below:

Column 1, line 41
"form" should be "formed"

Column 1, line 65
"inset" should be "insert"

Column 2, line 18
"4,762,132" should be "4,762,130"

Column 4, line 61
"is" should be "in"

Column 9, line 31
insert "to" after "extending"

Column 9, line 39
"second tube 186" should be "second tube 185"

Column 10, line 31
"that" should be "than"

UNITED STATES PATENT AND TRADEMARK OFFICE
CERTIFICATE OF CORRECTION

PATENT NO. : 5,156,620
DATED : Oct. 20, 1992
INVENTOR(S) : John P. Pigott

It is certified that error appears in the above-indentified patent and that said Letters Patent is hereby corrected as shown below:

Column 11, line 1, after "said", insert "apertures and said"

Signed and Sealed this

Twenty-eighth Day of September, 1993

Attest:

BRUCE LEHMAN

*Attesting Officer*   *Commissioner of Patents and Trademarks*